United States Patent [19]

Mikkelsen

[11] Patent Number: Plant 6,329

[45] Date of Patent: Oct. 11, 1988

[54] BEGONIA PLANT NAMED ST. HELENA

[75] Inventor: James C. Mikkelsen, Fripp Island, S.C.

[73] Assignee: Mikkelsens, Inc., Ashtabula, Ohio

[21] Appl. No.: 930,677

[22] Filed: Nov. 14, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Evans

[57] ABSTRACT

A begonia plant named St. Helena characterized by its large, double bright orange flowers; relatively large leaves with red tinged margins; early and long lasting flowering; strong stems and petioles, and compact growth, and by its ease of propagation from both stem and leaf cuttings.

1 Drawing Sheet

The present invention relates to a new and distinctive cultivar of begonia plant, botanically known as *hiemalis*×begonia, Fotsch, and known by the cultivar name St. Helena.

St. Helena was discovered in a cultivated area in Ashtabula, Ohio as a mutation of Stromboli (not patented), and was observed in a group of 10 cm flowering plants of the parent cultivar. The new cultivar was subsequently identified for development purposes by the designation 83-2436.

Asexual reproduction by stem and/or leaf cuttings by applicant has reproduced the unique features of the new cultivar through successive propagations.

The following characteristics are noted in reference to comparison cultivars, and the characteristics distinguish St. Helena from both its parent and other begonias commercially known and used in the floriculture industry:

1. In comparison to Stromboli which has a light orange flower, St. Helena is a brighter orange in color. Revelry (not patented) is a lighter orange and Tango, disclosed in U.S. Plant Pat. No. 5,538 is salmon orange in color.

2. The flower size of St. Helena is larger than Stromboli and Revelry and equal in size to Tango.

3. St. Helena is more double flowered than Stromboli and Revelry, and similar in that characteristic to Tango.

4. Plant size and shape of St. Helena is similar to Stromboli and Revelry, with Tango being more compact. The stems on St. Helena are very upright, similar to Revelry and Stromboli, with Tango having weaker flower stems.

5. The leaf margin of young leaves of St. Helena have a more pronounced red tinge than Stromboli, Tango and Revelry.

6. St. Helena has a reddish cast to the main stem, similar to Tango, with Revelry being greener and Stromboli having deep red stems.

7. Leaf texture is similar for all four cultivars; however, St. Helena has a slightly larger leaf than Tango, Revelry and Stromboli.

8. Strong stems and petioles and compact growth with good top flowering, making St. Helena suitable for 10, 15 and 25 cm pots.

9. St. Helena propagates readily from both stem and leaf cuttings.

The accompanying colored photograph illustrates in a top perspective view the overall appearance of St. Helena, with the colors being as true as it is reasonably possible to obtain in a colored reproduction of this type. The photograph was taken in late May 1986.

The following is a detailed description of my new begonia cultivar based on plants produced under commercial practices in Ashtabula, Ohio under greenhouse conditions. Color references are made to The Royal Horticultural Society Colour Chart except where general color terms of ordinary dictionary significance are used.

Parentage: Mutation from the cultivar Stromboli and identified as 83-2436.

Propagation:

(A) *Type cutting.*—Leaf cutting.

(B) *Time to root.*—18 days at 21° C. summer; 24 days at 21° C. winter.

(C) *Rooting habit.*—Abundant, fine, fibrous.

(D) *Time for shoot development.*—10 weeks in summer to 13 weeks in winter to obtain shoots 4 to 5 cm long in length.

Plant description:

(A) *Form.*—Upright, good stem strength for self-support; compact, short internodes; suitable for 10 and 15 cm pot plant production.

(B) *Habit of growth.*—Vigorous. Fast upright growth with good branching from base of plant when pinched. Usually vegetative shoots are formed at the basal nodes and flower shoots at the higher nodes.

(C) *Foliage.*—Leaves simple, alternate, borne on strong petioles 5–6 mm in diameter on mature leaves. (1) Size: Can vary greatly with leaf position on plant and number of shoots per plant. Environment can also effect leaf size; leaf is 10 to 12 cm across when mature. (2) Shape: Ovate to almost orbicular, lobes just touch on mature leaves. (3) Texture: Leathery, glabrous. (4) Margin: Serrated. (5) Color: Young foliage, top side 146B, with reddish tinge at margins. Young foliage, under side 146C at veins and red coloration on rest of surface. Mature foliage, top side 137A. Mature foliage, under side 148B. (6) Venation: Palmate; 6–7 major veins.

Flowering description:

(A) *Flowering habits.*—Flowering in racemes, 2 or 3 per raceme with several racemes in bloom at one time. Flowering continues more or less indefinitely.

(B) *Natural flowering season.*—Will flower year around without controlling daylength. Plants will flower earlier and more abundantly if subjected to a reduced daylength of 12 hours.

(C) *Flower buds.*—20 mm long and 30 mm wide just before opening. Tepals are entire around margins. Color 45D just before opening and 45C when immature.

(D) *Flowers borne.*—On strong upright peduncles ranging in color from green with faint red tint near main stem to reddish near flowers; 5 mm in diameter.

(E) *Quantity.*—Average of 3 per peduncle, opening in sequence as the raceme develops. Will vary with number of flowering shoots per plant.

(F) *Tepals.*—(1) Shape: Flat and nearly rounded. (2) Color top side in summer when opening: 32B, fading to 33C; under side 47C. (3) Number of tepals: 20 to 30 or more. (4) Size of tepals: 35 to 40 mm in diameter when open fully. (5) Flower size: 5 to 6 cm in diameter.

(G) *Reproductive organs.*—(1) Stamens: None as plant is fully double with anthers appearing as petals. (2) Pistels: None observed to date.

Disease resistance: St. Helena has shown good disease resistance to powdery mildew.

OTHER IMPORTANT CHARACTERISTICS

1. Early flowering. St. Helena can be finished in a 15 cm pot in 18 weeks from a stem cutting that is pinched.

2. Distinct large flowered, very double, bright orange-red flowers on strong upright growing stems.

3 Flowers are long lasting and fade to an acceptable color when old and do not shatter when shipped.

4. Propagates readily from stem and leaf cuttings and breaks well from a pinch.

5. Good balance between leaf size and plant size.

6. No female flowers and no pollen in the full double flowers.

I claim:

1. A new and distinct cultivar of begonia plant named St. Helena, as described and illustrated, and particularly characterized by its large, double bright orange flowers; relatively large leaves with red tinged margins; early and long lasting flowering; strong stems and petioles, and compact growth, and by its ease of propagation from both stem and leaf cuttings.

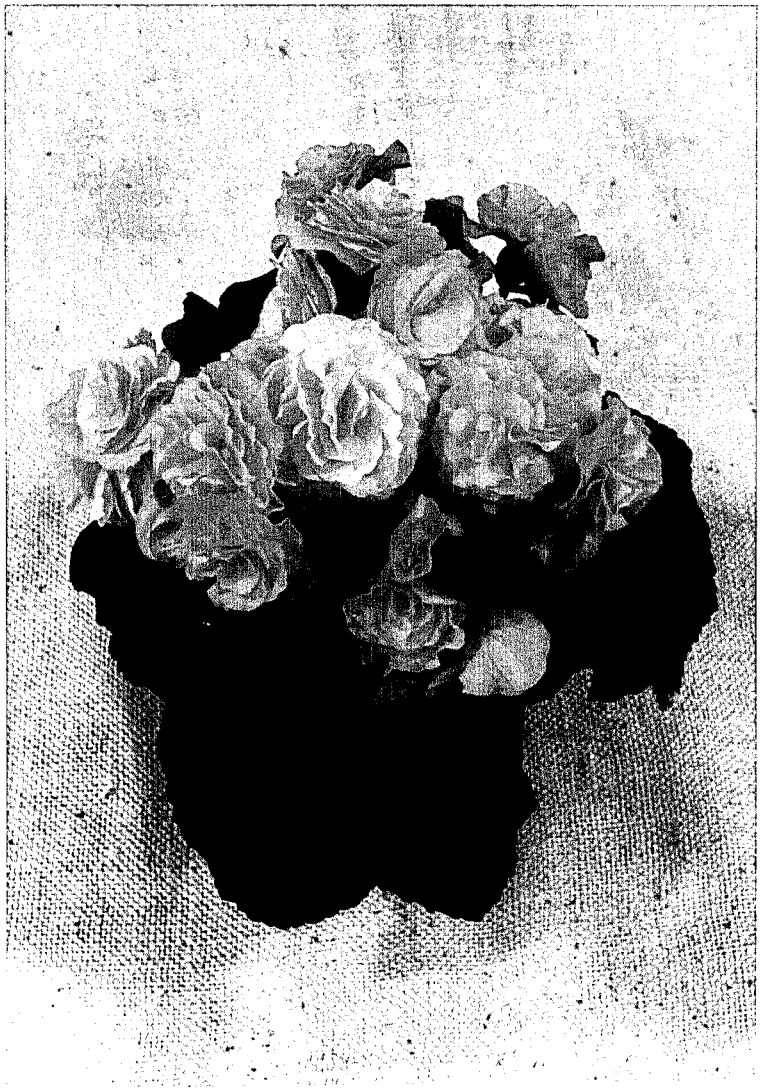

* * * * *